United States Patent [19]

Weiner

[11] Patent Number: 5,200,393

[45] Date of Patent: Apr. 6, 1993

[54] LIPID EXCIPIENT FOR NASAL DELIVERY AND TOPICAL APPLICATION

[75] Inventor: Alan L. Weiner, Lawrenceville, N.J.

[73] Assignee: The Liposome Company, Inc., Princeton, N.J.

[21] Appl. No.: 758,276

[22] Filed: Aug. 27, 1991

Related U.S. Application Data

[63] Continuation of Ser. No. 07/312,512, Feb. 17, 1989, abandoned.

[51] Int. Cl.$^5$ ................... A61K 37/02; A61K 47/44
[52] U.S. Cl. ........................... 514/3; 514/4; 554/80
[58] Field of Search .................. 514/3, 4; 260/403

[56] References Cited

U.S. PATENT DOCUMENTS

| | | | |
|---|---|---|---|
| 4,159,988 | 7/1979 | Eibl et al. | 260/403 |
| 4,338,306 | 7/1982 | Kitao et al. | 514/4 |
| 4,434,159 | 2/1984 | Sekine et al. | 514/3 |
| 4,619,795 | 10/1986 | Cohen | 424/1.1 X |
| 4,923,854 | 5/1990 | Tilcock et al. | 514/78 |

FOREIGN PATENT DOCUMENTS

| | | |
|---|---|---|
| 0285367 | 5/1988 | European Pat. Off. |
| 87/02219 | 4/1987 | World Int. Prop. O. |
| 87/04347 | 7/1987 | World Int. Prop. O. |
| 88/04556 | 6/1988 | World Int. Prop. O. |
| 88/09163 | 12/1988 | World Int. Prop. O. |

OTHER PUBLICATIONS

Duchateau, et al., "Influence of some surface-active agents on nasal absorption in rabbits", Int. J. Pharm. 39:87–92 (1987).
Gordon, et al., "Nasal absorption of insulin:Enhancement by hydrophobic bile salts", Proc. Natl. Acad. Sci. 82:7419–7423 (1985).
Hirai, et al., "Effect of surfactants on the nasal absorption of insulin in rats", Int. J. Pharm., 9:165–172 (1981).
Hirai, et al., "Mechanisms for the enhancement of the nasal absorption of insulin by surfactants", Inc. J. Pharm., 9:173–184 (1981).
Chemical Abstracts, vol. 108, 1988, Egi, et al., "Skin--treatment Products Containing Lysophosphalipids", p. 318, column 2, 226679p.
Chemical Abstracts, vol. 108, 1988, Togiya, et al., "Cosmetics Containing Oil-In-Polyhydric Alcohol Emulsions and Lysophospholipids which are Removable by Water", p. 321, column 1, 26827y.
259,988, Oct. 19, 1988, Janoff, Pending.
318,774, Mar. 3, 1989, Weiner, et al., Pending.
821,366, Jan. 22, 1986, Tilcock et al., Pending.

Primary Examiner—Jeffrey E. Russel
Assistant Examiner—Choon P. Koh
Attorney, Agent, or Firm—Allen Bloom; Catherine Kurtz Gowen

[57] ABSTRACT

Methods and compositions are described for liquid or gel forms of a lipid excipient to be used in pharmaceutical or cosmetic preparations. The lipid excipient comprises a phospholipid such as a lysophospholipid, for example, mono-oleoyl-phosphatidylethanolamine ("MOPE"). Relatively low concentrations of the lipid can be employed in forming the gel, e.g., about 1-2%. The invention discloses the use of a lipid delivery system at a relatively low lipid concentration as a non-toxic, non-irritating carrier or excipient alone or in combination with other agents, for both drugs and cosmetics. For example, the lipid excipient in sprayable or droppable form has special utility in the non-irritating delivery of peptides (e.g., calcitonin and insulin) to the nasal mucosa, due to the ability of the excipient to enhance absorption across nasal membranes. As a cosmetic, it can be used alone or in combination with biologically active agents.

23 Claims, 4 Drawing Sheets

LIPID EXCIPIENT FOR NASAL DELIVERY AND TOPICAL APPLICATION

This is a continuation of copending application Ser. No. 07/312,512 filed on Feb. 17, 1989, which is now abandoned.

BACKGROUND OF THE INVENTION

The present invention is directed to the field of delivery of drugs and cosmetics through administration with a lipid carrier. More particularly, the invention describes the use of lipids as surfactants and excipient delivery vehicles.

The topical (including ocular, nasal, aural, vaginal, dermal, and transdermal) delivery of biologically active agents such as drugs is typically achieved by the use of anionic, nonionic, amphoteric or cryptoanionic surfactants such as sodium deoxycholate or propylene glycol. This use of surfactants is due to the typically poor absorption of drugs or biological agents by this route; absorption being enhanced by use of these surfactants. Such surfactants, such as for example synthetic emulsifiers, form gels at certain concentrations, for example, at concentrations of about 14% to 75%, (Table 1) and are thereby used as carriers and excipients by the cosmetics industry. These concentrations of surfactants heretofore required are generally irritating to the nasal mucosa. In contrast, materials used to form liposomes are non-irritating, but have heretofore not been shown to enhance drug absorption across membranes. The present invention discloses the use of a lipid delivery system at a relatively low lipid concentration as a non-toxic, non-irritating carrier or excipient alone or in combination with other agents, for both drugs and cosmetics.

Previous work in the area of surfactants employed to enhance uptake of drugs involved the use of bile salts and other surfactants (Gordon et al., 1985, Proc. Natl. Acad. Sci. 82:7419-7423; Hirai et al., 1981, Int. J. Pharm., 9:165-172; Duchateau et al., 1987, Int. J. Pharm., 39:87-92; and Hanson et al., 1986 IN:Delivery Systems for Peptid Drug, Davis, ed., Plenum Press, N.Y., pp, 233-242). As stated hereinabove, these salts and surfactants have been found to be toxic to nasal mucosa (Hirai et al., 1981, Int. J. Pharm., 9:173-184).

The present invention discloses a new non-irritating lipid excipient system that can be used in liquid sprayable or droppable form, or alternatively in a viscous liquid or gel form. The physical state of the excipient (e.g., liquid, viscous liquid, or gel) depends on the lipid and concentration thereof used, the pH of the system, and the concentration of salts in the system. The lipid excipient in sprayable or droppable form has special utility in the non-irritating delivery of peptides (e.g., calcitonin and insulin) and hormones (e.g. growth hormone) to the nasal mucosa, due to the ability of the excipient to enhance peptide absorption across nasal membranes. This enhancement of absorption across membranes can also be characterized as an enhancement of the cell penetrating properties of the excipient, as compared to standard, more toxic excipients (e.g. deoxycholate), (see FIG. 3). In addition to the delivery of peptides, the excipient can also be used to deliver hormones, antihistimines and nasal moisturizers, among other biologically active agents. The dissolution or suspension of biologically active agents in the gel excipient of the invention can also provide a sustained release of the agent at the site of application.

With regard to topical delivery of pharmaceuticals or cosmetics, the same excipient, in viscous liquid or gel form, when applied to the skin surface exhibits the desirable "slip", "playtime", and "resonance" characteristics of a cosmetic preparation. As such, the preparations made with the lipid excipient of the invention can include the application of cosmetic preparations such as sunscreens e.g., para-amino benzoic acid (PABA), and moisturizers. As gel excipients for biologically active agents such as pharmaceuticals, the suspension or dissolution of the agent in the gel can serve as a sustained release medium for delivery of the agent across membranes. These gels can be applied intra-nasally, intra-ocularly, intra-aurally, buccally, dermally, transdermally, rectally, or vaginally.

The lipids employed in the present invention are preferably phospholipids, more preferably lysophospholipids. Lysophospholipids have heretofore been improbable candidates for pharmaceutical and cosmetic surfactants or excipients due to their lytic effects on cells. The present invention is directed to non-toxic, non-irritating compositions of pharmaceutical and cosmetic excipients comprising lysophosphatide, specifically lysophosphatidylethanolamine, more specifically mono-oleoyl-phosphatidylethanolamine ("MOPE").

SUMMARY OF THE INVENTION

The present invention is directed to a non-irritating lipid excipient which comprise a lysophospholipid, specifically mono-oleoyl phosphatidylethanolamine (MOPE). The excipient can be in a liquid or gel form, and can be formed with distilled water or salt solutions. When distilled water is employed, a liquid excipient is formed when the concentration of mono-oleoyl phosphatidylethanolamine is from about 0.1% to about 0.4%, and further wherein the pH of the excipient is about 8.5 to about 10.0, more preferably wherein the pH is about 9.0.

The excipient can also comprise a biologically active agent, for example, a peptide such as insulin or calcitonin. The excipient can alternatively be in a gel form, when the concentration of mono-oleoyl phosphatidylethanolamine is about 0.6% to about 2.0%, and the pH of the excipient is about 8.5 to about 10.0, preferably about pH 9.0. As a gel, the excipient can additionally comprise a biologically active agent, such as a peptide, for example insulin or calcitonin.

The excipient can alternatively be employed as a cosmetic, and can be used alone or can additionally comprise a biologically active agent. The cosmetic use of the lipid excipient of the invention can be as a liquid, viscous liquid or a gel.

DETAILED DESCRIPTION OF THE INVENTION

Figure 1:
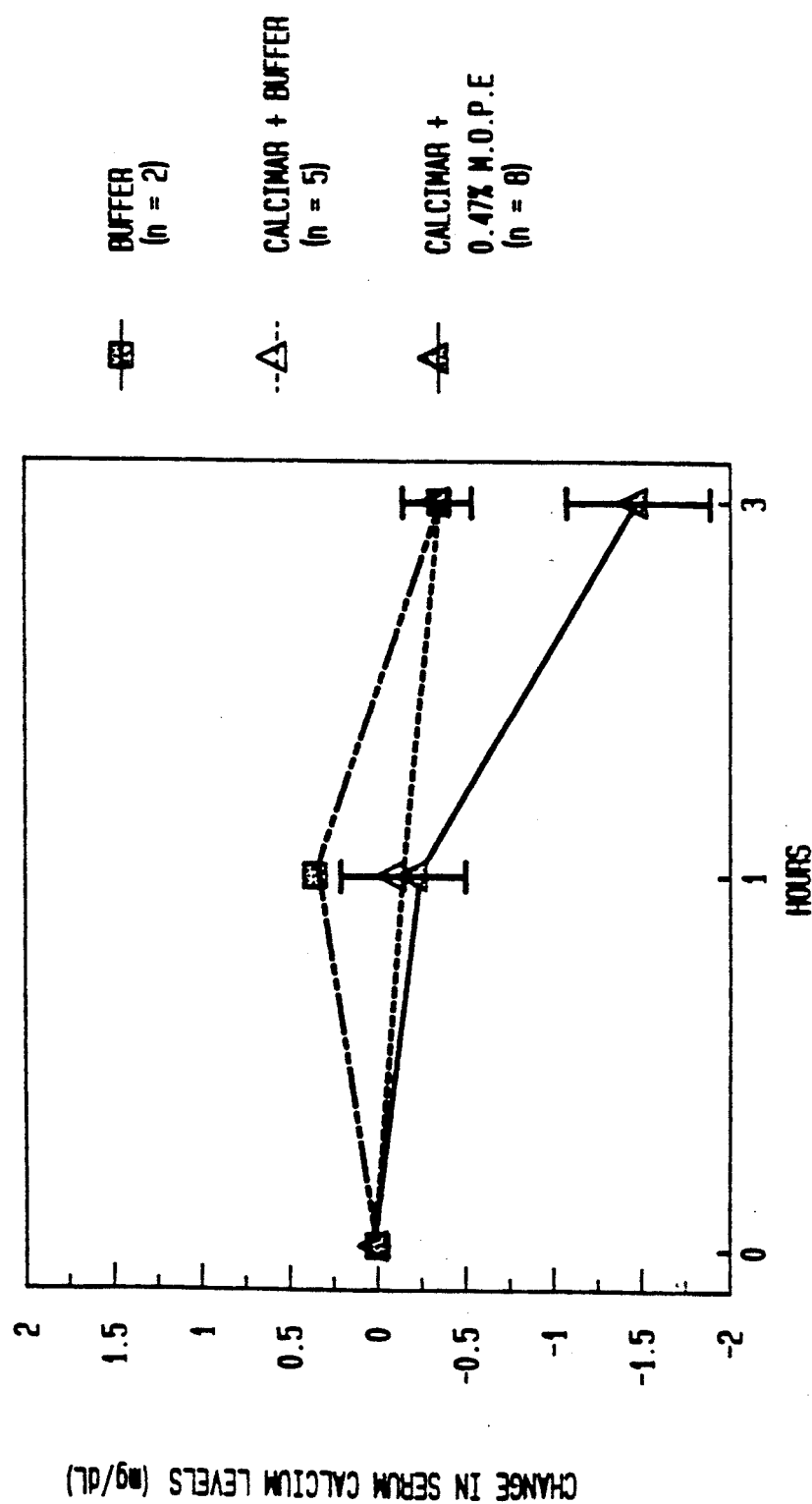
FIG. 1 is a graph showing the enhancement of calcitonin through the nasal mucosa when MPOE is used as the excipient delivery vehicle.

Lipids in relatively low concentrations can be used as surfactants and excipients in the present invention. The type of lipid, the amounts thereof employed, and the physical state of the excipient (e.g., sprayable or droppable liquid, viscous liquid or clear gel form) will depend upon the desired use and application. However, for the administration and delivery of biologically active agents e.g., an agent having biological activity, such as drugs, those types of lipids and amounts used will be those found to be sufficient to enhance the delivery and penetration of the drug across epithelial membranes such as the epidermis, dermis, or mucosa, e.g., nasal mucosa, while simultaneously being non-toxic and non-irritating. Such preparations may typically be in the form of droppable or sprayable liquids. However, a viscous liquid or a gel excipient may also exhibit desirable sustained release characteristics for a biologically active agent contained therein, or for a cosmetic.

In the case of cosmetics, those types and amounts of lipids used in the invention are those sufficient to produce a carrier or a gel for topical administration.

Many lipids can be employed as excipients in the present invention; most preferably used are the phospholipids, such as for example, phosphatidylcholines, phosphatidylethanolamines, and palmitoyl-oleoyl-phosphatidylethanolamine (POPE), and such as the anionic phospholipids such as for example phosphatidylserines and phosphatidylglycerols. Most preferably the lysophospholipids such as lysophosphatidylethanolamines are employed, for example, mono-oleoyl-phosphatidylethanolamine (MOPE), and mono-myristoyl-phosphatidylethanolamine (MMPE), but especially MOPE. Alternatively, the lysolipids mono-oleoyl-phosphatidic acid (MOPA), mono-oleoyl-phosphatidylserine (MOPS), and mono-oleoyl-phosphatidylglycerol (MOPG) can also be employed. Lysophosphatidylethanolamines having 2 or 3 double bonds such as sn-1-18:$2_{cis}$-PE and sn-1-18:$3_{cis}$-PE, respectively, can also be employed in the practice of the present invention. Alternatively, cardiolipin can be employed. Other lipids that can be used can be determined as such by their ability to enhance delivery of biologically active agents across membranes while at the same time, exhibiting minimal irritation, as measured for example by a standard red blood cell hemolysis test.

In the practice of the present invention, other lipids such as the steroidal lipid alpha-tocopherol hemisuccinate (THS) can be employed as a liquid excipient. A variety of tocopherols and their water soluble derivatives have been used to form liposomes, see Janoff et al., PCT Publication No. 87/02219, Apr. 23, 1987, entitled "Alpha Tocopherol-Based Vesicles." Applicants have also filed a U.S. patent application disclosing the use of alpha tocopherol hemisuccinate as a pharmaceutical delivery system wherein the THS is admixed with a stabilizer at low pH and the drug is thereafter associated with the THS. Janoff et al., U.S. patent appllication Ser. No. 259,988, filed Oct. 19, 1988, entitled "Tocopherol-Based Pharmaceutical Systems". In the instant invention, the biologically active agent can be delivered via a THS excipient by extrusion of a biologically active agent with the THS, forming SUVs. A particularly preferred method for forming SUVs is by the procedure described in Cullis et al., PCT Publication No. 87/00238, Jan. 16, 1986, entitled "Extrusion Technique for Producing Unilamellar Vesicles" incorporated herein by reference. Vesicles made by this technique are extruded under pressure through a membrane filter repetitively to form SUVs.

Both the liquid and the gel excipient can comprise the lipid MOPE. 1-oleoyl lysophosphatidylethanolamine (MOPE) may be expressed as:

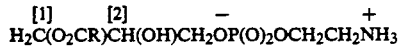

$$H_2C(O_2CR)CH(OH)CH_2OP(O)_2OCH_2CH_2NH_3$$

wherein R is the oleoyl group attached to the carbon in the 1-position, as labeled [1], thus 1-oleoyl. The (OH) group is located on the [2] carbon. This lipid may be further expressesd as sn-1-18:$1_{cis}$-PE, denoting the 18 carbon composition of the oleoyl group, followed by a number denoting the number of double bonds, in ths case 1 double bond in ths cis configuration. As a further illustration of the nomenclature, for example, more highly unsaturated Lyso PEs (LOPEs), wherein R is in the 1-position and has 2 or 3 double bonds and 17 carbon atoms; are expressed as sn-1-18:$2_{cis}$-PE and sn-1-18:$3_{cis}$-PE, respectively. The carboxylate carbon atom is the 18th carbon atom.

We have previously disclosed that 1-oleoyl lysophosphatidylethanolamine (MOPE, or sn-1-18:$1_{cis}$-PE) exhibits a lamellar phase at physiological pH rather than the micellar arrangement of other lysophospholipids. Tilcock et al., U.S. patent application No. 821,366, filed Jan. 22, 1986, entitled "Solubilization of Hydrophobic Materials Using Lysophospholipids." MOPE, however, exhibits a micellar state at higher pH (e.g., at about 8.5 or higher) which promotes micellar solubilization of hydrophobic substances under such conditions. This polymorphic phase behavior from micellar to bilayer states is substantiated by: (a) $^{31}$P-NMR spectra, which correspond to a lamellar configuration at pH 7 at temperatures of $-20°$ C. to $90°$ C., in contrast to lysophosphatidylcholine which is micellar; (b) x-ray diffraction patterns of MOPE, in which the x-ray scatter forms equidistantly spaced rings, indicative of a lamellar organization; (c) freeze fracture micrographs which show the multilamellar nature of liposomes produced at pH 8.2; and (d) $^{31}$P-NMR spectra that show isotropic motional averaging at pH 9.0, indicative of a micellar structure. We have previously disclosed that the micellar to bilayer phase transition of lysophospholipids can be used to dissolve hydrophobic agents (Tilcock et al., 1986, Biochemistry, Vol. 25(4):816–822).

MOPE at pH 9.0 (adjusted with sodium hydroxide or sodium bicarbonate) hydrated alternatively with distilled water or dilute salt concentrations (e.g., up to about 0.5M salt, for example) ranges from a clear liquid of droppable or sprayable consistency at a concentration of about 0.1% to about 0.4%, and increases in viscosity from about 0.4% to 2.0%, at which concentration it is a clear gel. For penetration enhancement of insulin, the concentration that has most efficacy is 0.2% MOPE, at pH 9.0, in distilled water.

MOPE at pH 9.0 (adjusted with sodium hydroxide or sodium bicarbonate) and at salt concentrations up to about 0.5M, at concentrations of MOPE from about 0.1% to about 2.0% are throughout these concentrations a cloudy fluid.

For the formation of the sprayable or droppable liquid excipient, the lipid (e.g., the lysophospholipid, for example, MOPE) is admixed with solutions of low ionic content e.g., distilled water or dilute salt solutions of less than about 0.5M, at temperatures of about 5° C. to about 90° C., preferably at about 20°–3020 C., most preferably about 25° C., at pH between about 8.5 and about 14.0, more preferably about pH 8.5 to about pH 10.0, most preferably about pH 9.0, at a lipid concentration between about 0.1% and about 0.4%, preferably a lipid concentration of about 0.2% to about 0.3%, most preferably about 0.2%. Following mixture of the lipid into the aqueous solution, the biologically active agent can be admixed therein, to a biologically active agent concentration limited only by the solubility of the agent in the system, or limited by the desired concentration in the resulting suspension; for calcitonin, for example, to a concentration of about 100 U/ml. Most preferably, the aqueous solution employed is distilled water, but may alternatively be a solution containing salts, such as for example a buffer or saline solution. In this case, the salt concentration can be as high as about 0.5M. When salts are employed with the lipid excipient, the excipient takes the form of a cloudy fluid.

Alternatively, the lipid can be suspended at pH about 6.0 to about 8.2, preferably about pH 7.0 in solutions such as distilled water or alternatively solutions containing salts in any concentration. When the excipient solution is at about pH 7.0, regardless of the aqueous composition and the lipid concentration, the excipient takes the form of a cloudy fluid. In the case of insulin, enhanced drug absorption occurs at a lipid concentration of about 0.8%.

For the formation of the gel excipient, the lipid (e.g., the lysophospholipid, for example, MOPE) is admixed with distilled water at a temperature of about 5° C. to about 90° C., preferably about 25° C., at a pH between about 8.2 and about 14.0, more preferably between about 8.5 and about 10.0, most preferably about pH 9.0, at a lipid concentration between about 0.4% (for a relatively loose gel), and about 10% or above, a stiffer gel being formed at a lipid concentration of about 2% lipid and above. Following admixture of the lipid and water, the biologically active agent can be admixed to a concentration determined only by the solubility of the drug in the gel, or alternatively by the desired concentration of the drug suspension in the gel. When salts are employed with the lipid excipient at pH 9.0 or thereabouts and at lipid concentrations of about 0.6% to about 2.0%, the excipient takes the form of a cloudy fluid.

The lipid excipient or carrier of the present invention may be admixed with a biologically active agent such as for example, a drug, hormone, protein, dye, vitamin, or imaging agent. As used in the present invention, the terms biologically active agent and bio active agent are used interchangeably, and are understood to include any compound having biological activity; e.g., drugs and other therapeutic agents such as peptides, hormones, toxins, enzymes, neurotransmitters, lipoproteins, glycoproteins, immunomodulators, immunoglobulins, polysaccharides, cell receptor binding molecules, nucleic acids, polynucleotides, and the like, as well as biological tracer substances such as dyes, radio-opaque agents, and fluorescent agents.

The biologically active agents may be either hydrophobic or hydrophilic; where they are hydrophobic, the lipid excipient (e.g., the MOPE) of the invention can be employed to solubilize the agent according to the methods of copending U.S. patent application to Tilcock et al., U.S. Ser. No. 821,366, filed Jan. 22, 1986, entitled "Solubilization of Hydrophobic Materials Using Lysophospholipids." More specifically, the hydrophobic and hydrophilic agents include but are not limited to the polyene antibiotics such as the anti-fungal agents pimaricin, candicidin, filipin, and preferably, nystatin and amphotericin B. Other biologically active agents that may be used include but are not limited to antibacterial compounds such as the aminoglycosides, for example, gentamicin, antiviral compounds such as rifampacin, anti-parasitic compounds such as antimony derivatives, antineoplastic compounds such as vinblastine, vincristine, mitomycin C, doxorubicin, daunorubicin, methotrexate, and cisplatin, among others, proteins such as albumin, toxins such as diptheria toxin, enzymes such as catalase, hormones such as estrogens, neurotransmitters such as acetylcholine, lipoproteins, such as alpha-lipoprotein, glycoproteins such as hyaluronic acid, immunoglobulins such as IgG, immunomodulators such as the interferons or the interleukins, dyes such as Arsenazo III, radiolabels such as $^{14}C$, radio-opaque compounds such as $^{99}Te$, fluorescent compounds such as carboxy fluoroscein, polysaccharides such as glycogen, cell receptor binding molecules such as estrogen receptor protein, nonsteroidal anti-inflammatories such as indomethacin, salicylic acid acetate, ibuprofen, sulindac, piroxicam, and naproxen; anti-inflammatories such as dexamethasone, antiglaucomic agents such as timolol or pilocarpine, anesthetics such as dibucaine, nucleic acids such as thymine, polynucleotides such as RNA polymers, cardiovascular agents such as alpha-blocker, beta-blocker, calcium channel blockers, ACE inhibitors, and the like, CNS agents, and prostaglandins.

The salt solutions that can be employed in the lipid excipients of the invention include but are not limited to physiological saline, Ringers and other saline solutions, buffers such as carbonate buffer, methylglucamine, N-2-hydroxyethyl piperazine-N-2-ethane sulfonic acid (HEPES), ethylenediminetetraacetic acid (EDTA), and tris(hydroxymethyl)aminomethane (Tris). Such salt or buffer solutions can be employed in concentrations of up to about 0.5M salt.

For the topical mode of administration, the lipid excipient, alone or together with a biologically active or other inert agent, may be administered to the surface of the skin, or administered via another route, e.g., nasal, vaginal, intraocular, buccal, rectal, or intra-aural. For such applications, the lipid excipient can be delivered in its sprayable or droppable liquid form or alternatively in its gel form.

When the mode of administration is intra-ocular or intra-aural, the suspensions can be delivered by delivery systems known in the art such as for example single or multidose droppers or applicators. The ocular compositions can further contain mucomimetics such as hyaluronic acid, chondroitin sulfate, hydroxypropyl methylcellulose, or polyvinyl alcohol; and preservatives, such as sorbic acid EDTA or benzylchonium chloride, and the usual quantities of diluents and/or carrier materials. When the mode of administration is nasal, a spray delivery device such as a container or other vessel that allows instillation of a measured dosage can be employed.

The biologically active agent formulations employing the lipid excipients of the present invention can be used therapeutically in mammals, including man, in the treatment of infections or other conditions which benefit from the enhanced delivery of the drug in its biologically active form. For administration to humans in the curative treatment of disease states, the prescribing physician will ultimately determine the appropriate dosage for a given human subject, and this can be expected to vary according to the age, weight, and response of the individual as well as the nature and severity of the patient's disease.

With regard to topical delivery of cosmetics, the lipid excipient, in viscous liquid or gel form, when applied to the skin surface exhibits the desirable "slip", "playtime", and "resonance" characteristics of a cosmetic preparation. When used as a cosmetic preparation, the lipid excipients can be applied to the skin alone or in combination with biologically active or other agents (e.g., such as perfumes, paraffins, oils, coloring agents, glycerins) to improve the surface characteristics, e.g., texture and elasticity, of the skin thereby reducing dryness or dehydration, thereby avoiding the onset of dry lines and wrinkles, and other visible signs of aging.

Other preparations made with the lipid excipient of the invention can include the cosmetic preparations such as sunscreens e.g., para-amino benzoic acid (PABA), and moisturizers. For cosmetic applications, the formulations can be administered at will or according to standard practice.

The following examples are given for purposes of illustration only and not by way of limitation on the scope of the invention.

EXAMPLE 1

MOPE (8.0 mg) in chloroform was dried down to a lipid film on a round bottom flask at 37° C. in a water bath. The film was resuspended in 1.0 ml of distilled water which had been pH adjusted to pH 9.0 with about 20-50 uL of 0.1N sodium hydroxide (NaOH). One ml of calcitonin (supplied as Calcimar, USV, Tuckahoe, N.Y., as a 200 U/ml solution) was added to the resuspended MOPE and the solution vortically mixed for about 15 seconds. The pH was readjusted to pH 9.0 with 0.1N NaOH.

EXAMPLE 2

The methods of Example 1 were employed using 4.0 mg of MOPE, resulting in a 0.2% MOPE solution.

EXAMPLE 3

Eight Wistar Kyoto male rats, weighing 250-300 g were anesthetized with a 20% solution of urethane administered in a divided dose of 1/6 g/kg, administered intraperitoneally (IP).

The rats were surgically prepared for nasal sample instillation according to the Harai method (Hussain et al., 19800, J. Pharm. Sci., 69(12):1411-1413. A pre-drug blood sample was taken from each rat (1.0 ml drawn from retroorbital site) and allowed to clot, and the serum separated by standard technique.

The calcitonin-MOPE solution (single 50 uL doses per rate) were administered by inserting a syringe containing the sample into the rats nostril, and injecting. A blood sample was obtained from each rat after one and three hours, and assayed for serum calcium.

Serum calcium was determined colorimetrically by the Sigma Diagnostics Calcium Kit No. 587 (Sigma, St. Louis, Mo.). The change in serum calcium levels compared to pre-drug controls was plotted as a function of time. (FIG. 1)

EXAMPLE 4

MOPE (40.0 mg) in chloroform was dried down to a lipid film on a round bottom flask at 37° C. in a water bath. The film was resuspended in 10.0 ml of distilled water which had been pH adjusted to pH 9.0 with about 20-50 uL of 0.1N sodium hydroxide (NaOH). Four mg of porcine insulin power (Eli Lilly, Indianapolis, Ind.) supplied as 25 U/mg, was admixed with the MOPE solution and vortically mixed.

EXAMPLE 5

The insulin-MOPE solution of Example 4 was instilled into the nasal cavity of rats according to the methods of Example 3. Right Sprague-Dawley male 300 g rats which had been made diabetic according to the methods of Weiner et al., 1985, J. Pharm. Sci., 74:922-925 were used. Blood samples were collected after one hour and serum separated according to standard methods as in Example 3. The serum was analyzed for insulin using the Coat-A-Count Insulin $^{125}$I radioimmunoassay (Diagnostic Products Corp., Los Angeles, Calif.).

EXAMPLE 6

Figure 2:
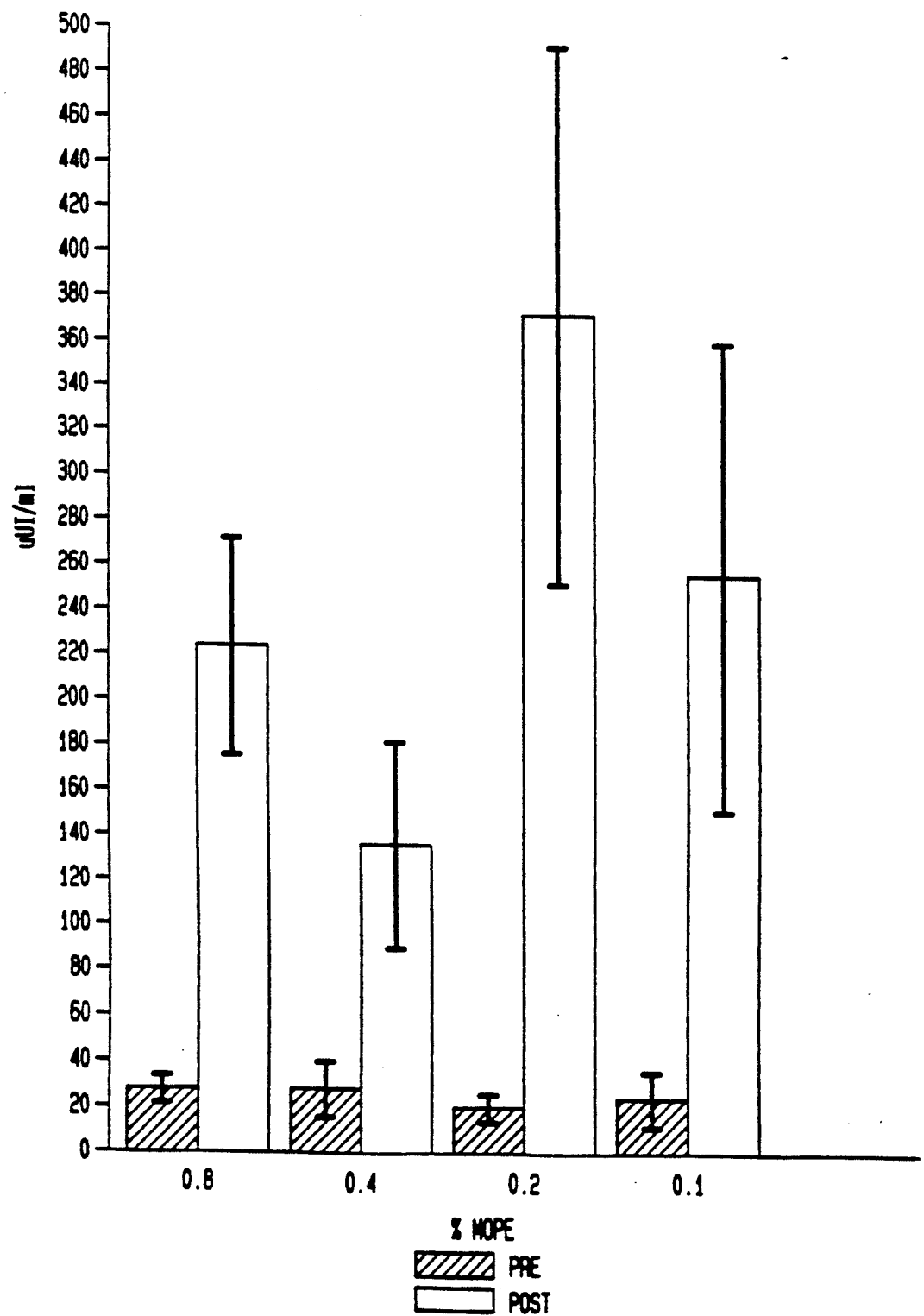
FIG. 2 is a histogram showing the nasal delivery of insulin administered with 0.1%, 0.2%, 0.4%, and 0.8% MOPE solutions. At 0.8% MOPE, the excipient is a loose gel.

MOPE (80.0 mg) in chloroform was dried down to a lipid film on a round bottom flask at 37° C. in a water bath. The film was resuspended in 10.0 ml of distilled water which had been pH adjusted to pH 9.0 with about 20-50 uL of 0.1N sodium hydroxide (NaOH). Four mg of porcine insulin powder (Eli Lilly, Indianapolis, Ind.) supplied as 25 U/mg, was admixed with the MOPE solution and vortically mixed, creating a 0.8% MOPE insulin gel. The resulting gel was administered to diabetic rats according to the methods of Example 5. Blood was drawn one hour post insulin-MOPE administration, and the results of the serum insulin concentratoin assay was plot against MOPE concentration as seen in FIG. 2. The methods of the above Example were repeated, dilutions were made to result in 10 ml of each of 0.4%, 0.2%, and 0.1% MOPE, 4.0 mg of insulin being admixed with these MOPE samples as well, the complete results from serum insulin concentrations of each sample plotted together in FIG. 2.

EXAMPLE 7

A one percent deoxycholate (Sigman, St. Louis, Mo.) solution was prepared in distilled water in a total of 10 ml. Four mg of insulin was admixed and vortically mixed to dissolve, resulting in a 0.5 U insulin solution.

Figure 3:
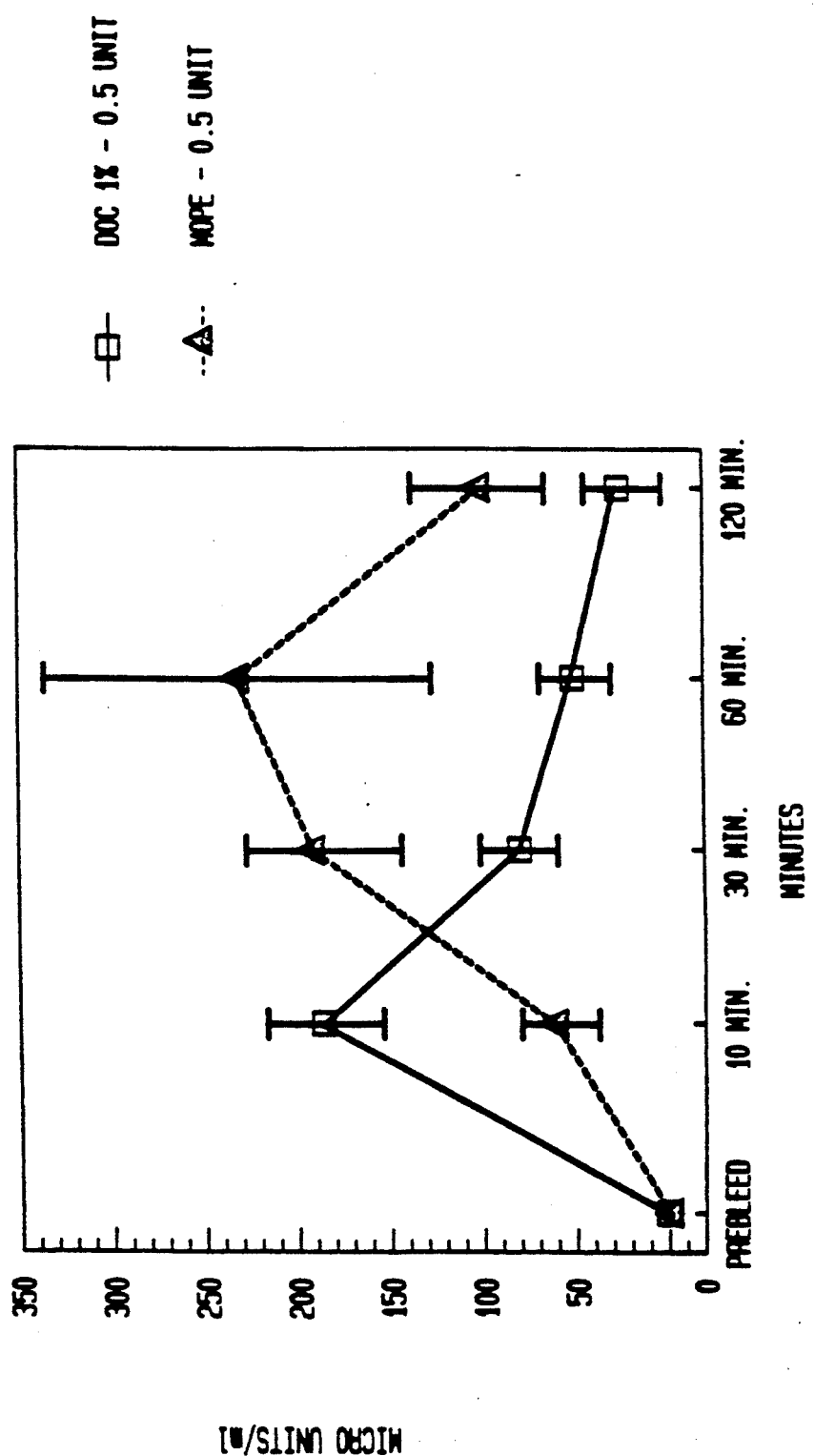
FIG. 3 is a graph showing the change in blood insulin levels after administration of insulin in deoxycholate and MOPE.

This insulin-deoxycholate solution was surgically instilled in rats according to the procedures of Example 3. Serum insulin was analyzed using the Coat-A-Count radioimmunoassay kit as in Example 5. Results are shown in FIG. 3.

EXAMPLE 8

Figure 4:
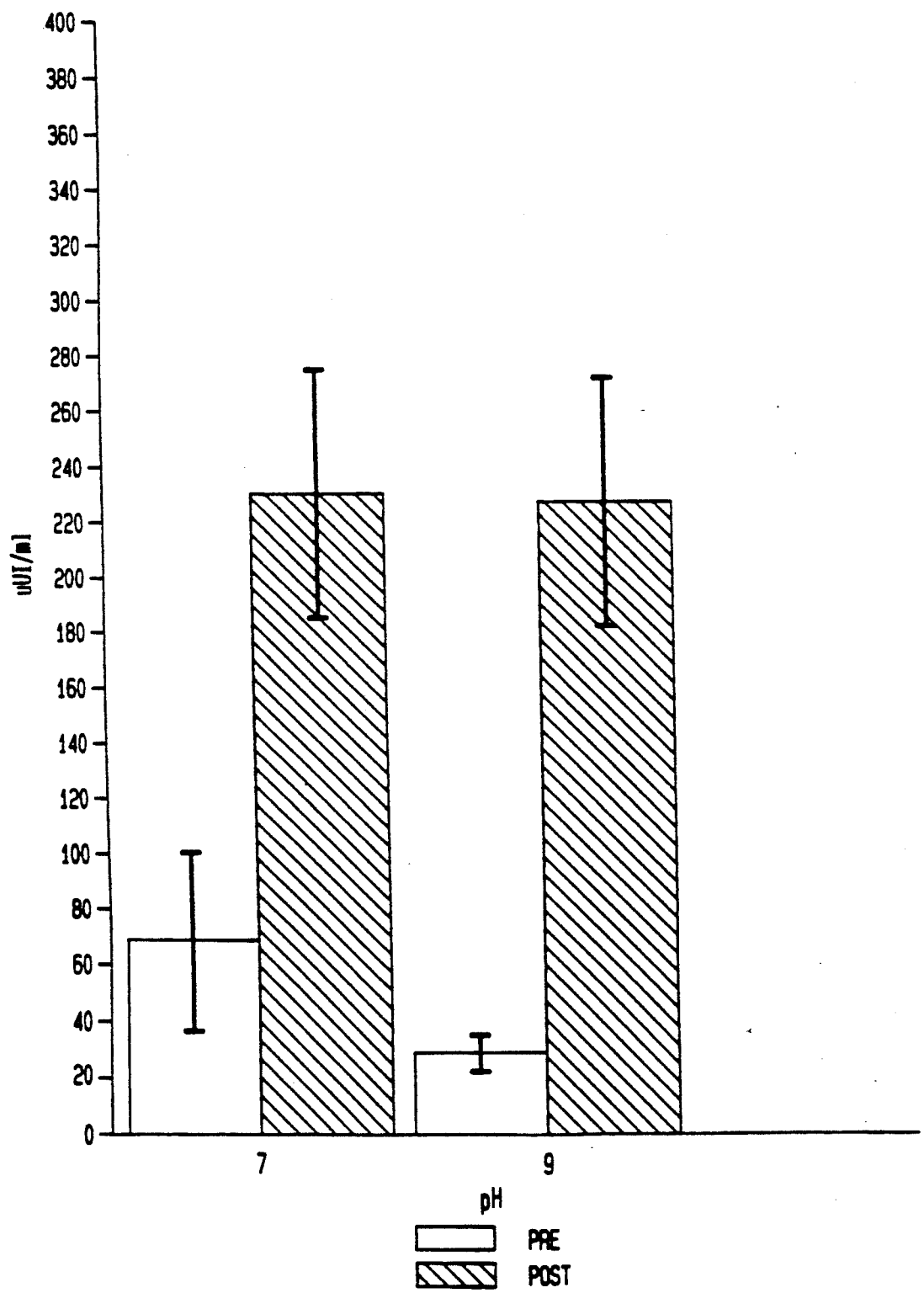
FIG. 4 is a histogram of 0.8% MOPE employed as excipient at pH 7 and pH 9 to deliver insulin intranasally in the rat.

MOPE (80.0 mg) in chloroform was dried down to a lipid film on a round bottom flask at 37° C. in a water bath. The film was resuspended in 10.0 ml of distilled water which had been pH adjusted to pH 7.0 with about 20-50 uL of 0.1N sodium hydroxide (NaOH). Four mg of porcine insulin powder (Eli Lilly, Indianapolis, Ind.) supplied as 25 U/mg, was admixed with the MOPE solution and vortically mixed, creating a 0.8% MOPE insulin solution. The sample was administered to diabetic rats according to the methods of Example 5. Blood was drawn one hour post insulin-MOPE administration, and the results of the serum insulin concentration assay was plotted against MOPE system pH as seen in FIG. 4.

EXAMPLE 9

MOPE (50.0 mg) in chloroform was dried down to a lipid film on a round bottom flask at 37° C. in a water bath. The film was resuspended in 5.0 ml of distilled water which had been pH adjusted to pH 9.0 with about 20-50 uL of 0.1N sodium hydroxide (NaOH).

TABLE 1

The following is a partial list of surfactants which are either supplied or can form gels at the given concentration:

| Surfactant | Company | Emulsifier Type | Charge* | Concentration |
|---|---|---|---|---|
| Tauranol T-Gel | Finetex | Sodium N-Methyl-N-oleoyltaurate | A | 14% |
| Igepon T-51 | GAF | Same as above | | |
| Incromine Oxide I | Croda | Isostearamidopropyl dimethylamine oxide | N | 25% |
| Incromine Oxide 0 | Croda | Oleamidopropyl-dimethylamine oxide | N | 25% |
| Sandopan OLS | Sandoz | Ethoxylated Anionic Complex | A | 30% |
| Brij 78 | ICI | Polyoxyethylene 20 Stearyl Ether | N | 35% |
| Schercotaine PAB | Scher Chemical | Palmitylamido Betaine 20 oleyl ether | Amp | 35% |
| Lanamine | Amerchol | Amine | A | 50% |
| Lanogel | Amerchol | Polyoxyalkylene Lanolins | N | 50% |
| Tergelan 1790 | Emery | Alkylamine Lanoline Derivative | A | 50% |
| Ampho-terge W2 | Lonza | Imidazoline Amphoteric Dicarboxylic Sodium salt | A | 52% |
| Surfine WNT or WCT Gel | Finetex | Carboxylate Type | CA | 60% |
| Miranate LEC | Miranol | Sodium Laureth-13 Carboxylate | A | 70% |
| Sandopan DTC | Sandoz | Ethoxylated Anionic Complex | A | 70% |
| Crestolan | Chemos | Ethylene oxide Carboxylate | A | 75% |
| Magicrest | Chemos | Sulfated nonionic | A | 75% |
| J-Pongel | Sybron | Taurate | A | ? |

*A = Anionic
Amp = Amphoteric
CA = Cryptoanionic
N = Nonionic

What is claimed is:

1. A non-irritating lipid vesicle excipient composition comprising mono-oleoyl phosphatidylethanolamine vesicles, a salt solution, and a water soluble protein or peptide wherein the composition has a pH from about 8.5 to about 10.0 and a concentration of mono-oleoyl phosphatidylethanolamine of about 0.1 to 0.4 weight %, wherein the excipient is adapted for mucosal delivery.

2. The excipient of claim 1 wherein the pH of the excipient is about 9.0.

3. The excipient of claim 2 wherein the peptide is insulin.

4. The excipient of claim 2 wherein the peptide is calcitonin.

5. The composition of claim 1 wherein the water soluble protein or peptide is a cosmetic.

6. A non-irritating gel lipid excipient composition comprising mono-oleoyl phosphatidylethanolamine, aqueous solution of low ionic content and a water soluble protein or peptide wherein the composition has a pH of from about 8.5 to about 10.0 and a concentration of mono-oleoyl phosphatidylethanolamine of from about 0.4% about 2.0 weight % wherein the excipient is adapted for mucosal delivery.

7. The composition of claim 6 wherein aqueous solution is water or dilute salt concentrations of up to about 0.5M salt.

8. The composition of claim 7 wherein the pH of the composition is about 9.0.

9. The composition of claim 8 wherein the peptide is insulin or calcitonin.

10. A non-irritating lamellar lipid excipient composition comprising mono-oleoyl phosphatidylethanolamine, aqueous solution and a water soluble protein or peptide wherein the composition has a pH of from about 6.0 to about 8.2, wherein the excipient is adapted for mucosal delivery.

11. The composition of claim 10 wherein aqueous solution is water or a salt solution.

12. The composition of claim 11 wherein the pH of the composition is about 7.0.

13. The composition of claim 12 wherein the peptide

14. The composition of claim 13 wherein the MOPE concentration is from about 0.1 to 0.4 weight % and wherein the salt solution is of low ionic content.

15. The composition of claim 13 wherein the MOPE concentration is from about 0.4 to 2.0 weight % and wherein the salt concentration is greater than about 0.5M.

16. A non-irritating lamellar lipid excipient comprising mono-oleoyl phosphatidylethanolamine, aqueous solution and a water soluble protein or peptide wherein the composition has a pH of from about 8.5 to about 10.0, and wherein the excipient is adapted for mucosal delivery.

17. The composition of claim 16 wherein the MOPE concentration is from about 0.4 to 2.0 weight % and wherein the salt concentration is greater than about 0.5M.

18. The composition of claim 17 wherein the pH of the composition is about 9.0.

19. The composition of claim 18 wherein the protein or peptide is insulin or calcitonin.

20. A non-irritating micellar lipid excipient composition comprising mono-oleoyl phosphatidylethanolamine, aqueous solution of low ionic content and a water soluble protein or peptide wherein the composition has a pH of from about 8.5 to about 10.0 and a concentration of mono-oleoyl phosphatidylethanolamine of from about 0.1% to about 0.4%, wherein the excipient is adapted for mucosal delivery.

21. The composition of claim 20 wherein the pH of the composition is about 9.0.

22. The composition of claim 21 wherein the peptide is insulin or calcitonin.

23. A non-irritating micellar lipid excipient composition comprising mono-oleoyl phosphatidylethanolamine, water and insulin, wherein the composition has a pH of about 9.0 and a mono-oleoyl phosphatidylethanolamine concentration of about 0.2%.

* * * * *